United States Patent
Hashimoto et al.

(10) Patent No.: US 10,035,752 B2
(45) Date of Patent: Jul. 31, 2018

(54) MULTIFUNCTIONAL (METH)ACRYLATE MANUFACTURING METHOD

(71) Applicant: TOAGOSEI CO., LTD., Tokyo (JP)

(72) Inventors: Naoki Hashimoto, Nagoya (JP); Shuuhei Yamaguchi, Nagoya (JP); Motoo Ootsuka, Nagoya (JP)

(73) Assignee: TOAGOSEI CO., LTD., Tokyo (JP)

( * ) Notice: Subject to any disclaimer, the term of this patent is extended or adjusted under 35 U.S.C. 154(b) by 0 days.

(21) Appl. No.: 15/302,061

(22) PCT Filed: Mar. 10, 2015

(86) PCT No.: PCT/JP2015/056888
§ 371 (c)(1),
(2) Date: Oct. 5, 2016

(87) PCT Pub. No.: WO2015/159611
PCT Pub. Date: Oct. 22, 2015

(65) Prior Publication Data
US 2017/0204044 A1 Jul. 20, 2017

(30) Foreign Application Priority Data
Apr. 16, 2014 (JP) .................................. 2014-084174

(51) Int. Cl.
| | | |
|---|---|---|
| *B01J 31/04* | (2006.01) | |
| *C07C 67/03* | (2006.01) | |
| *B01J 31/02* | (2006.01) | |
| *B01J 35/00* | (2006.01) | |
| *C07C 213/06* | (2006.01) | |
| *C07D 251/30* | (2006.01) | |

(52) U.S. Cl.
CPC ........... *C07C 67/03* (2013.01); *B01J 31/0237* (2013.01); *B01J 31/0244* (2013.01); *B01J 31/04* (2013.01); *B01J 35/0006* (2013.01); *C07C 213/06* (2013.01); *C07D 251/30* (2013.01); *B01J 2231/49* (2013.01); *B01J 2531/002* (2013.01); *B01J 2531/26* (2013.01)

(58) Field of Classification Search
CPC ..... B01J 31/04; B01J 31/0237; B01J 31/0244
See application file for complete search history.

(56) References Cited

U.S. PATENT DOCUMENTS

| | | | | |
|---|---|---|---|---|
| 3,787,479 A | * | 1/1974 | Grehl ...................... | C07C 67/03 422/213 |
| 2003/0055203 A1 | | 3/2003 | Ooga et al. | |
| 2003/0144460 A1 | | 7/2003 | Ooga et al. | |

FOREIGN PATENT DOCUMENTS

| | | |
|---|---|---|
| JP | S53105417 A | 9/1978 |
| JP | 200269035 A | 3/2002 |
| JP | 2003190819 A | 7/2003 |
| JP | 2005298404 A | 10/2005 |
| JP | 4591733 B2 | 12/2010 |
| JP | 4656351 B2 | 3/2011 |

OTHER PUBLICATIONS

Maegawa, Y. et al., "Additive Effective of N-heteroaromatice on Transesterification Catalyzed by Tetranuclear Zinc Cluster, ACS Catalysis", vol. 1, No. 10, 2001, p. 1178-1182.
International Search Report dated May 12, 2015, dated Jun. 9, 2015.
English Translation of International Search Report dated May 12, 2015, dated Jun. 9, 2015.

\* cited by examiner

*Primary Examiner* — Pancham Bakshi
(74) *Attorney, Agent, or Firm* — Norris McLaughlin & Marcus P.A.

(57) ABSTRACT

[Problem] The purpose of the present invention is to obtain a multifunctional (meth)acrylate with good yield by an ester exchange reaction of a polyhydric alcohol such as pentaerythritol or dipentaerythritol with a monofunctional (meth)acrylate.
[Solution] A multifunctional (meth)acrylate manufacturing method characterized in that when manufacturing a multifunctional (meth)acrylate by an ester exchange reaction of a polyhydric alcohol with a monofunctional (meth)acrylate, catalyst (A) and catalyst (B) are used together. Catalyst (A): One or more kinds of compounds selected from a group consisting of cyclic tertiary amines with an azabicyclo structure or salts or complexes thereof, amidines or salts or complexes thereof, and compounds with a pyridine ring or salts or complexes thereof. Catalyst (B): One or more kinds of compounds selected from a group consisting of zinc-containing compounds.

9 Claims, 1 Drawing Sheet

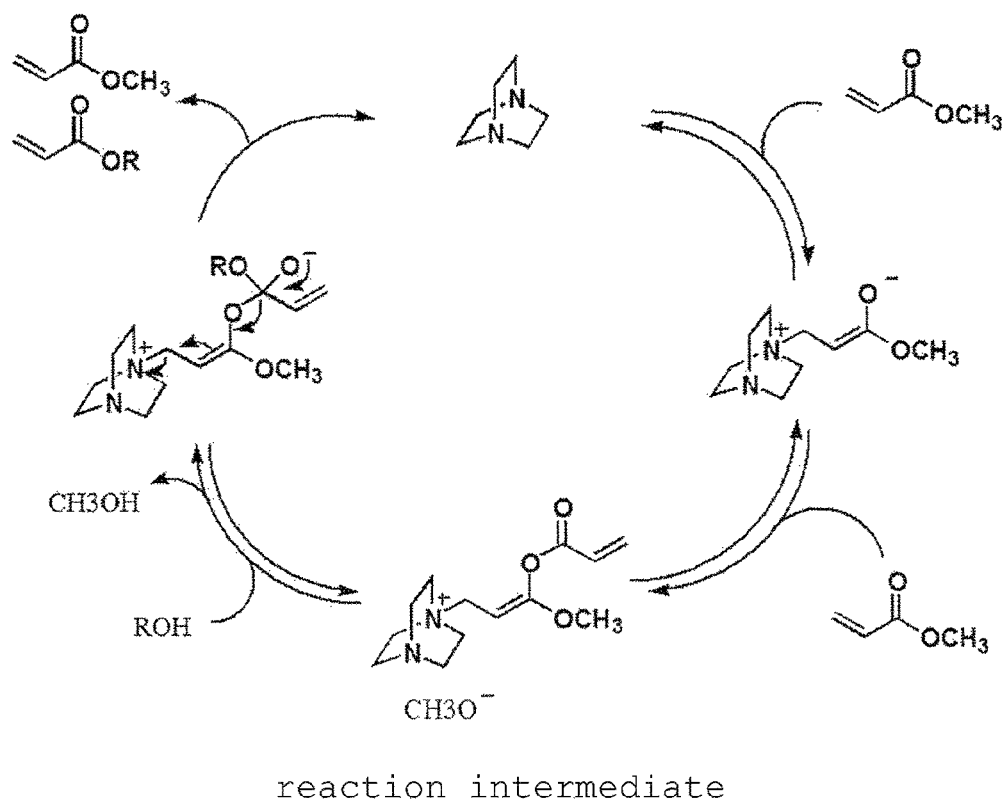
reaction intermediate

MULTIFUNCTIONAL (METH)ACRYLATE MANUFACTURING METHOD

This application is a 371 application of PCT/JP2015/056888 filed Mar. 10, 2015, which claims foreign priority benefits under 35 U.S.C. § 119 of Japanese Application No. 2014-084174 filed Apr. 16, 2014, the disclosures of each of which are incorporated by reference herein in their entirety.

TECHNICAL FIELD

The present invention relates to a multifunctional (meth)acrylate manufacturing method. More specifically, the present invention relates to a multifunctional (meth)acrylate manufacturing method which is characterized in that a multifunctional (meth)acrylate is obtained based on a transesterification of a polyhydric alcohol with a monofunctional (meth)acrylate.

BACKGROUND ART

Since (meth)acrylate can be cured by irradiation of active energy rays such as ultraviolet rays or electron beam, (meth)acrylate is used in a large amount as a cross-linking component in paint, ink, adhesives, optical lens, a filling agent, and a blend like a molding material, or as a reactive diluent component.

In particular, as a blending component of a hard coat paint, a multifunctional (meth)acrylate having 3 or more (meth)acryloyl groups is used in a large amount since a cured product thereof exhibits high hardness and excellent abrasion resistance.

As for the multifunctional (meth)acrylate, trimethylolpropane tri(meth)acrylate, glycerin tri(meth)acrylate, pentaerythritol tri(meth)acrylate, pentaerythritol tetra(meth)acrylate, ditrimethylolpropane tetra(meth)acrylate, dipentaerythritol tetra(meth)acrylate, dipentaerythritol penta(meth)acrylate, dipentaerythritol hexa(meth)acrylate, tripentaerythritol octa(meth)acrylate, and the like are known.

Those multifunctional (meth)acrylates have been manufactured by an esterification reaction between a corresponding polyhydric alcohol and a (meth)acrylic acid or a transesterification.

For manufacturing a multifunctional (meth)acrylate based on an esterification reaction, sulfonic acid such as sulfuric acid, paratoluenesulfonic acid, or methanesulfonic acid is used as a catalyst. However, to remove the corresponding sulfonic acid from a crude reaction product, which is obtained after completion of the esterification reaction, it is necessary to perform extraction washing using an aqueous alkali solution. As such, the processes are complicated and a marked decrease in productivity is observed. There is also a problem that, as part of the target multifunctional acrylate is saponified during the extracting operation, a decrease in yield is caused.

Meanwhile, for manufacturing a multifunctional (meth)acrylate based on a transesterification, it is possible to have a progress of the reaction without using sulfonic acid, and a method of using an organotin compound as a catalyst (see, Patent Literature 1), a method of using in combination a zinc compound and an organophosphorus compound as a catalyst (see, Patent Literature 2), and the like are known.

However, although those methods of using a catalyst have high yield of a multifunctional (meth)acrylate, from the viewpoint of a harmful property of catalyst, it is necessary to have a purification operation for reducing as possible the catalyst remained in a product. In particular, when a multifunctional (meth)acrylate having 3 or more (meth)acryloyl groups is manufactured by using a polyhydric alcohol having 3 or more alcoholic hydroxyl groups as a raw material, from the viewpoint that the multifunctional (meth)acrylate has extremely low vapor pressure so that it is difficult to be purified and obtained as a distillation component by distillation, a purification operation like liquid-liquid extraction needs to be performed several times and a decrease in productivity is marked due to complicated processes (see, Patent Literature 1). In addition, since there is a case in which high cost is required for detoxification of wastes that are generated in conjunction with purification, it is difficult to say that the method is an economically advantageous method.

Although a method of having a titanium compound with relatively low toxicity as a catalyst for a transesterification is known (see, Patent Literature 3), according to knowledge of the inventors of the present invention, the yield is very low when a polyhydric alcohol having 3 or more alcoholic hydroxyl groups is applied as a raw material for manufacture of a multifunctional (meth)acrylate having 3 or more (meth)acryloyl groups.

CITATION LIST

Patent Literature

Patent Literature 1: JP 2003-190819 A (Claims)
Patent Literature 2: Japanese Patent No. 4656351
Patent Literature 3: Japanese Patent No. 4591733

SUMMARY OF INVENTION

Technical Problem

The present invention is devised under the current circumstances described above and the present invention relates to a multifunctional (meth)acrylate manufacturing method, and an object thereof is to obtain a multifunctional (meth)acrylate with good yield by a transesterification of a polyhydric alcohol with a monofunctional (meth)acrylate while not using a catalyst with high toxicity such as an organotin compound or an organophosphorus compound.

Solution to Problem

To solve the problems described above, the inventors of the present invention conducted intensive studies. As a result, it was found that, by using the following catalyst A and catalyst B in combination for manufacturing a multifunctional (meth)acrylate by a transesterification of a polyhydric alcohol with a monofunctional (meth)acrylate, the multifunctional (meth)acrylate can be obtained with good yield. The present invention is completed accordingly.

Catalyst A: One or more kinds of compounds selected from the group consisting of cyclic tertiary amines with an azabicyclo structure or salts or complexes thereof, amidines or salts or complexes thereof, and compounds with a pyridine ring or salts or complexes thereof.

Catalyst B: One or more kinds of compounds selected from the group consisting of zinc-containing compounds.

Advantageous Effects of Invention

According to the manufacturing method of the present invention, a multifunctional (meth)acrylate can be obtained with good yield.

The multifunctional (meth)acrylate obtained by the manufacturing method of the present invention can be preferably used for various industrial applications as a cross-linking component in paint, ink, adhesives, optical lens, a filling agent, and a blend like a molding material, or as a reactive diluent component.

BRIEF DESCRIPTION OF DRAWINGS

FIG. 1 is a schematic view illustrating the reaction pathway related to the multifunctional (meth)acrylate manufacturing method of the present invention.

DESCRIPTION OF EMBODIMENTS

The present invention relates to obtaining a multifunctional (meth)acrylate with good yield by using in combination the following catalyst A and catalyst B during manufacture of a multifunctional (meth)acrylate according to a transesterification of a polyhydric alcohol with a monofunctional (meth)acrylate.

Catalyst A: One or more kinds of compounds selected from the group consisting of cyclic tertiary amines with an azabicyclo structure or salts or complexes thereof, amidines or salts or complexes thereof, and compounds with a pyridine ring or salts or complexes thereof.

Catalyst B: One or more kinds of compounds selected from the group consisting of zinc-containing compounds.

Hereinbelow, the present invention is described in detail.

The polyhydric alcohol which is used as a raw material in the present invention is an aliphatic alcohol, an alicyclic alcohol, an aromatic alcohol, a polyhydric alcohol ether, and the like which have 2 or more alcoholic hydroxyl groups in the molecule, and they may have, in the molecule, other functional group or bond, for example, a phenolic hydroxyl group, a ketone group, an acyl group, an aldehyde group, a thiol group, an amino group, an imino group, a cyano group, a nitro group, an ether bond, an ester bond, an amide bond, an imide bond, a peptide bond, a urethane bond, an acetal bond, a hemiacetal bond, a hemiketal bond, and the like.

Specific examples of the dihydric alcohol having 2 alcoholic hydroxyl groups include ethylene glycol, diethylene glycol, triethylene glycol, polyethylene glycol, propylene glycol, trimethylene glycol, dipropylene glycol, tripropylene glycol, polypropylene glycol, butanediol, pentanediol, hexanediol, heptanediol, nonanediol, neopentylglycol, cyclohexanediol, cyclohexanedimethanol, dioxane glycol, N-methyldiethanolamine, N-ethyldiethanolamine, N-butyldiethanolamine, N-tert-butyldiethanolamine, N-lauryldiethanolamine, stearyldiethanolamine, N-phenyldiethanolamine, m-tolyldiethanolamine, p-tolyldiethanolamine, N,N'-bis(2-hydroxypropyl)aniline, N-nitrosodiethanolamine, N-(2-hydroxyethyl)lactamide, N,N'-bis(2-hydroxyethyl)oxamide, 3-morpholino-1,2-propanediol, 2,6-pyridinedimethanol, 3-(dimethylamino)-1,2-propanediol, 3-(diethylamino)-1,2-propanediol, alloxantin dihydrate, (+)-N,N,N',N'-tetramethyl-L-tartaric acid diamide, (−)-N,N,N',N'-tetramethyl-D-tartaric acid diamide, N-propyl-N-(2,3-dihydroxypropyl)perfluoro-n-octyl sulfonamide, thymidine, chloramphenicol, thiamphenicol, D-erythronolactone, methyl 4,6-O-benzylidene-α-D-glucopyranoside, phenyl 4,6-O-benzylidene-1-thio-β-D-glucopyranoside, 1,2:5,6-di-O-isopropylidene-D-mannitol, 1,2-O-isopropylidene-α-D-xylofuranose, 2,6-di-O-palmitoyl-L-ascorbic acid, isoorbide, and alkylene oxide adducts thereof, and also alkylene oxide adducts of a compound having phenolic hydroxyl group such as hydroquinone, bisphenol A, bisphenol AP, bisphenol AF, bisphenol B, bisphenol BP, bisphenol C, bisphenol E, bisphenol F, bisphenol G, bisphenol M, bisphenol S, thio bisphenol, bisphenol P, bisphenol PH, bisphenol TMC, or bisphenol Z.

Specific examples of the trihydric alcohol having 3 alcoholic hydroxyl groups include trimethylolethane, trimethylolpropane, glycerin, tris(2-hydroxyethyl)isocyanurate, hexanetriol, octanetriol, decanetriol, triethanolamine, triisopropanolamine, 1-[bis 2-(hydroxyethyl)amino]-2-propanol, D-panthenol, DL-panthenol, uridine, 5-methyluridine, cytidine, inosinic acid, adenosine, leucomycin A3, leucomycin A4, leucomycin A6, leucomycin A8, hydrochloric acid clindamycin monohydrate, prednisolone, methyl β-D-arabinopyranoside, methyl β-L-fucopyranoside, methyl α-L-fucopyranoside, D-galactal, 4-methoxyphenyl3-O-allyl-β-D-galactopyranoside, 4-methoxyphenyl3-O-benzyl-β-D-galactopyranoside, 1,6-anhydro-β-D-glucose, α-chloralose, β-chloralose, 4,6-O-ethylidene-α-D-glucopyranose, D-glucal, 1,2-O-isopropylidene-α-D-glucofuranose, D-glucurono-6,3-lactone, 2-Deoxy-D-ribose, methyl β-D-ribofuranoside, D-(+)-ribono-1,4-lactone, methyl-β-D-xylopyranoside, 6-O-palmitoyl-L-ascorbic acid, 6-O-stearoyl-L-ascorbic acid, 3-O-ethyl-L-ascorbic acid, and alkylene oxide adducts thereof.

Specific examples of the tetrahydric alcohol having 4 alcoholic hydroxyl groups include ditrimethylolethane, ditrimethylolpropane, diglycerin, pentaerythritol, N,N,N',N'-tetrakis(2-hydroxyethyl)butanediamide, N,N,N',N'-tetrakis(2-hydroxypropyl)butanediamide, N,N,N',N'-tetrakis(2-hydroxyethyl)hexanediamide, N,N,N',N'-tetrakis(2-hydroxypropyl)hexanediamide, N,N,N',N'-tetrakis(2-hydroxyethyl)ethylenediamine, N,N,N',N'-tetrakis(2-hydroxypropyl)ethylenediamine, N-hexanoyl-D-glucosamine, N-valeryl-D-glucosamine, N-trifluoroacetyl-D-glucosamine, N-benzoyl-D-glucosamine, 5-acetamide-N,N'-bis(2,3-dihydroxypropyl)-2,4,6-triiodoisophthalamide, spiramycin, clarithromycin, leucomycin A1, leucomycin A5, leucomycin A7, leucomycin A9, leucomycin A13, lyncomycin hydrochloride monohydrate, diazolidinyl urea, D-(−)-arabinose, DL-arabinose, L-(+)-arabinose, meso-erythritol, D-(+)-fucose, L-(−)-fucose, allyl α-D-galactopyranoside, methyl β-D-galactopyranoside, methyl α-D-galactopyranoside monohydrate, 4-methoxyphenyl β-D-galactopyranoside, 2-nitrophenyl β-D-galactopyranoside, 4-nitrophenyl α-D-galactopyranoside, 4-nitrophenyl β-D-galactopyranoside, phenyl β-D-galactopyranoside, N-acetyl-D-galactosamine hydrate, D-(+)-galactosamine hydrochloride, albutin, 2-deoxy-D-glucose, esculin 1.5 hydrate, D-(+)-glucono-1,5-lactone, D-glucuronic amide, helicin, methyl α-D-glucopyranoside, methyl β-D-glucopyranoside 0.5 hydrate, 4-methoxyphenyl β-D-glucopyranoside, 4-nitrophenyl β-D-glucopyranoside monohydrate, 4-nitrophenyl α-D-glucopyranoside, nonyl β-D-glucopyranoside, n-octyl β-D-glucopyranoside, phenyl β-D-glucopyranoside hydrate, phlorhizin hydrate, piceid, puerarin, N-acetyl-D-glucosamine, N-benzoyl-D-glucosamine, D-(+)-glucosamine hydrochloride, N-hexanoyl-D-glucosamine, N-valeryl-D-glucosamine, L-(+)-gulonic acid γ-lactone, D-(−)-lyxose, L-(+)-lyxose, 3,4-O-isopropylidene-D-mannitol, methyl α-D-mannopyranoside, D-mannono-1,4-lactone, 4-methoxyphenyl α-D-mannopyranoside, N-acetyl-D-mannosamine monohydrate, D-(−)-ribose, L-ribose, D-(+)-xylose, DL-xylose, L-(−)-xylose, D-araboascorbic acid, L-ascorbic acid, L-threitol, and alkylene oxide adducts thereof.

Specific examples of the pentahydric alcohol having 5 alcoholic hydroxyl groups include tritrimethylolethane, tritrimethylolpropane, triglycerol, bis(2-hydroxyethyl)amino tris(hydroxymethyl)methane, bis(2-hydroxypropyl)amino tris(hydroxymethyl)methane, N,N,N',N'', N''-pentakis(2-hydroxyethyl)diethylene triamine, N,N,N',N'', N''-pentakis(2-hydroxypropyl)diethylene triamine, miglitol, erythromycin, azithromycin dihydrate, D-(+)-arabitol, DL-arabitol, L-(−)-arabitol, D-(−)-fructose, L-(+)-fructose, D-(+)-galactose, L-(−)-galactose, β-D-glucose, D-(+)-glucose, L-(−)-glucose, D-glucose diethyl mercaptal, salicin, L-gulose, D-(+)-mannose, L-(−)-mannose, ribitol, L-(−)-sorbose, D-tagatose, xylitol, sucralose, glyceryl ascorbic acid, and alkylene oxide adducts thereof.

Specific examples of the polyhydric alcohol having 6 or more alcoholic hydroxyl groups include polytrimethylolethane, polytrimethylolpropane, polyglycerin, dipentaerythritol, tripentaerythritol, polypentaerythritol, iohexol, galactinol, D-sorbitol, L-sorbitol, myo-unositol, scyllo-unositol, D-mannitol, L-mannitol, icariin, amygdalin, D-(+)-cellobiose, geosmin, 2-O-α-D-glucopyranosyl-L-ascorbic acid, hesperidin, D-(+)-lactose monohydrate, lactulose, D-(+)-maltose monohydrate, D-(+)-melibiose monohydrate, methyl hesperidin, maltitol, naringin hydrate, neohesperidin dihydrohcalcone hydrate, palatinose hydrate, rutin hydrate, D-(+)-sucrose, stevioside, D-(+)-turanose, D-(+)-trehalose (anhydrous), D-(+)-trehalose dihydrate, D-(+)-melezitose hydrate, D-(+)-raffinose pentahydrate, rebaudioside A, stachyose, α-cyclodextrin, β-cyclodextrin, γ-cyclodextrin, starch, and alkylene oxide adducts thereof.

In the present invention, those polyhydric alcohols may be used either singly or in combination of two or more types. Among those polyhydric alcohols, a polyhydric alcohol having 3 or more alcoholic hydroxyl groups is preferable. In particular, trimethylolethane, trimethylolpropane, glycerin, alkylene oxide adduct of glycerin, tris(2-hydroxyethyl)isocyanurate, triethanolamine, ditrimethylolethane, ditrimethylolpropane, diglycerin, alkylene oxide adduct of diglycerin, pentaerythritol, alkylene oxide adduct of pentaerythritol, xylitol, alkylene oxide adduct of dipentaerythritol, dipentaerythritol, and D-sorbitol are preferable. Furthermore, if a hydrate or a solvate is present for those polyhydric alcohols, the hydrate and solvate can be also used as a polyhydric alcohol for the manufacturing method of the present invention.

The monofunctional (meth)acrylate used as a raw material in the present invention is a compound which has one (meth)acryloyl group in the molecule, and examples thereof include a compound represented by the following General Formula (1).

[Chem. 1]

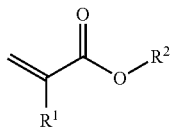

(1)

In the formula, $R^1$ represents a hydrogen atom or a methyl group. $R^2$ represents an organic group with 1 to 50 carbon atoms.

Specific examples of $R^2$ in the above General Formula (1) include a methyl group, an ethyl group, a n- or i-propyl group, a n-, i- or t-butyl group, a n-, s- or t-amyl group, a neopentyl group, a n-, s- or t-hexyl group, a n-, s- or t-heptyl group, a n-, s- or t-octyl group, a 2-ethylhexyl group, a capryl group, a nonyl group, a decyl group, a undecyl group, a lauryl group, a tridecyl group, a myristyl group, a pentadecyl group, a cetyl group, a heptadecyl group, a stearyl group, a nonadecyl group, an alkyl group, ceryl group, a myricyl group, a mellisyl group, a vinyl group, an allyl group, a metallyl group, a crotyl group, a 1,1-dimethyl-2-propenyl group, a 2-methyl butenyl group, a 3-methyl-2-butenyl group, a 3-methyl-3-butenyl group, a 2-methyl-3-butenyl group, a butenyl group, a pentenyl group, a hexenyl group, a heptenyl group, an octenyl group, a nonenyl group, a decenyl group, a undecenyl group, a dodecenyl group, a tridecenyl group, a tetra decenyl group, a pentadecenyl group, a hexa decenyl group, a heptadecenyl group, an oleyl group, a linol group, a linolene group, a cyclopentyl group, a cyclopentyl methyl group, a cyclohexyl group, a cyclohexylmethyl group, a 4-methylcyclo hexyl group, a 4-t-butylcyclohexyl group, a tricyclodecanyl group, an isobornyl group, an adamantyl group, a dicyclopentanyl group, a dicyclopentenyl group, a phenyl group, a methylphenyl group, a dimethyl phenyl group, a trimethylphenyl group, a 4-t-butylphenyl group, a benzyl group, a diphenylmethyl group, a diphenylethyl group, a triphenylmethyl group, a cinnamyl group, a naphthyl group, an anthranyl group, a methoxyethyl group, a methoxyethoxyethyl group, a methoxyethoxyethoxyethyl group, a 3-methoxybutyl group, an ethoxyethyl group, an ethoxyethoxyethyl group, a cyclopentoxyethyl group, a cyclohexyloxyethyl group, a cyclopentoxyethoxyethyl group, a cyclohexyloxyethoxyethyl group, a dicyclopentenyloxyethyl group, a phenoxyethyl group, a phenoxyethoxyethyl group, a glycidyl group, a β-methylglycidyl group, a β-ethylglycidyl group, a 3,4-epoxycyclohexylmethyl group, a 2-oxetanemethyl group, a 3-methyl-3-oxetanemethyl group, a 3-ethyl-3-oxetanemethyl group, a tetrahydrofuranyl group, a tetrahydrofurfuryl group, a tetrahydropyranyl group, a dioxazolanyl group, a dioxanyl group, an N,N-dimethylaminoethyl group, an N,N-diethylaminoethyl group, an N,N-dimethylaminopropyl group, an N,N-diethylaminopropyl group, an N-benzyl-N-methylaminoethyl group, and an N-benzyl-N-methylaminopropyl group.

In the present invention, those monofunctional (meth)acrylates may be used either singly or in combination of two or more types. Among those monofunctional (meth)acrylate, methyl acrylate, ethyl acrylate, n-butyl acrylate, i-butyl acrylate, 2-ethylhexyl acrylate, 2-methoxyethyl acrylate, and 2-dimethylaminoethyl acrylate are preferable. In particular, methyl acrylate, ethyl acrylate, n-butyl acrylate, i-butyl acrylate, and 2-methoxyethyl acrylate, which exhibit good reactivity for most polyhydric alcohols and are easily obtainable, are preferable. Furthermore, it is more preferably 2-methoxyethyl acrylate which promotes dissolution of polyhydric alcohol and exhibits very good reactivity.

The use ratio of the polyhydric alcohol and monofunctional (meth)acrylate for the manufacturing method of the present invention is not particularly limited. However, the monofunctional (meth)acrylate is used preferably at from 0.4 to 10.0 mole and more preferably at from 0.6 to 5.0 mole per mole of hydroxyl group in the polyhydric alcohol. If the monofunctional (meth)acrylate is less than 0.4 mole, more side reactions are caused. If it is more than 10.0 mole, the production amount of multifunctional (meth)acrylate is small and the productivity is poor.

According to the manufacturing method of the present invention, it is possible to perform the reaction without using a solvent. However, a solvent may be used, if necessary, and specific examples thereof include hydrocarbons such as n-hexane, cyclohexane, methylcyclohexane, n-heptane, n-octane, n-nonane, n-decane, benzene, toluene, xylene, ethylbenzene, diethylbenzene, isopropylbenzene, amylbenzene, diamylbenzene, triamylbenzene, dodecylbenzene, didodecylbenzene, amyltoluene, isopropyltoluene, decalin, or tetralin, ethers such as diethyl ether, dipropyl ether, diisopropyl ether, dibutyl ether, diamyl ether, diethylacetal, dihexyl acetal, t-butylmethyl ether, cyclopentyl methyl ether, tetrahydrofuran, tetrahydropyran, trioxane, dioxane, anisole, diphenyl ether, dimethyl cellosolve, diglyme, triglyme, or tetraglyme, crown ethers such as 18-crown-6, alcohols such as methanol, ethanol, n-propanol, i-propanol, n-butanol, i-butanol, t-butanol, ethylene glycol, 2-methoxyethanol, or glycerin, esters such as methyl benzoic acid or γ-butyrolactone, ketones such as acetone, methyl ethyl ketone, methyl isobutyl ketone, cyclohexanone, acetophenone, or benzophenone, sulfones such as sulfolane, sulfoxides such as dimethyl sulfoxide, ureas or derivatives thereof, phosphine oxides such as tributylphosphine oxide, ionic liquid such as imidazolium salt, piperidinium salt, or pyridinium salt, silicone oil, and water. Among those solvents, hydrocarbons, ethers, alcohols, and ion liquid are preferable. Those solvents may be used either singly or in combination of two or more types.

The catalyst A for the manufacturing method of the present invention is one or more kinds of compounds that are selected from the group consisting of cyclic tertiary amines with an azabicyclo structure or salts or complexes thereof, amidines or salts or complexes thereof, and compounds with a pyridine ring or salts or complexes thereof.

Specific examples of the cyclic tertiary amines with an azabicyclo structure or salts or complexes thereof include 1-azabicyclo[1,1,0]butane, 1,3-diazabicyclo[1,1,0]butane, 1-azabicyclo[2,1,0]heptane, 1,3-diazabicyclo[2,1,0]heptane, 1,4-diazabicyclo[2,1,0]heptane, 1-azabicyclo[2,2,0]hexane, 1,3-diazabicyclo[2,2,0]hexane, 1-azabicyclo[2,1,1]hexane, 1,3-diazabicyclo[2,1,1]hexane, 1-azabicyclo[2,2,1]heptane, 1,3-diazabicyclo[2,2,1]heptane, 1,4-diazabicyclo[2,2,1]heptane, 1-azabicyclo[3,2,0]heptane, 1,3-diazabicyclo[3,2,0]heptane, 1,4-diazabicyclo[3,2,0]heptane, 1,6-diazabicyclo[3,2,0]heptane, 1,3-diazabicyclo[2,2,2]octane, 1-azabicyclo[3,2,1]octane, 1,3-diazabicyclo[3,2,1]octane, 1,4-diazabicyclo[3,2,1]octane, 1,5-diazabicyclo[3,2,1]octane, 1,6-diazabicyclo[3,2,1]octane, 1-azabicyclo[4,1,1]octane, 1,3-diazabicyclo[4,1,1]octane, 1,4-diazabicyclo[4,1,1]octane, 1,5-diazabicyclo[4,1,1]octane, 1,6-diazabicyclo[4,1,1]octane, 1,7-diazabicyclo[4,1,1]octane, 1-azabicyclo[4,2,0]octane, 1,3-diazabicyclo[4,2,0]octane, 1,4-diazabicyclo[4,2,0]octane, 1,5-diazabicyclo[4,2,0]octane, 1,7-diazabicyclo[4,2,0]octane, 1-azabicyclo[3,3,1]nonane, 1,3-diazabicyclo[3,3,1]nonane, 1,4-diazabicyclo[3,3,1]nonane, 1,5-diazabicyclo[3,3,1]nonane, 1-azabicyclo[3,2,2]nonane, 1,3-diazabicyclo[3,2,2]nonane, 1,4-diazabicyclo[3,2,2]nonane, 1,5-diazabicyclo[3,2,2]nonane, 1,6-diazabicyclo[3,2,2]nonane, 1,8-diazabicyclo[3,2,2]nonane, 1-azabicyclo[4,3,0]nonane, 1,3-diazabicyclo[4,3,0]nonane, 1,4-diazabicyclo[4,3,0]nonane, 1,5-diazabicyclo[4,3,0]nonane, 1,6-diazabicyclo[4,3,0]nonane, 1,7-diazabicyclo[4,3,0]nonane, 1,8-diazabicyclo[4,3,0]nonane, 1-azabicyclo[4,2,1]nonane, 1,3-diazabicyclo[4,2,1]nonane, 1,4-diazabicyclo[4,2,1]nonane, 1,5-diazabicyclo[4,2,1]nonane, 1,6-diazabicyclo[4,2,1]nonane, 1,7-diazabicyclo[4,2,1]nonane, 1-azabicyclo[5,2,0]nonane, 1,3-diazabicyclo[5,2,0]nonane, 1,3-diazabicyclo[5,2,0]nonane, 1,4-diazabicyclo[5,2,0]nonane, 1,5-diazabicyclo[5,2,0]nonane, 1,6-diazabicyclo[5,2,0]nonane, 1,7-diazabicyclo[5,2,0]nonane, 1,8-diazabicyclo[5,2,0]nonane, 1-azabicyclo[5,1,1]nonane, 1,3-azabicyclo[5,1,1]nonane, 1,4-azabicyclo[5,1,1]nonane, 1,5-azabicyclo[5,1,1]nonane, 1,6-azabicyclo[5,1,1]nonane, 1,7-azabicyclo[5,1,1]nonane, 1-azabicyclo[6,1,0]nonane, 1,3-diazabicyclo[6,1,0]nonane, 1,4-diazabicyclo[6,1,0]nonane, 1,5-diazabicyclo[6,1,0]nonane, 1,6-diazabicyclo[6,1,0]nonane, 1,7-diazabicyclo[6,1,0]nonane, 1,8-diazabicyclo[6,1,0]nonane, 1-azabicyclo[7,1,0]decane, 1,9-diazabicyclo[7,1,0]decane, 1-azabicyclo[6,2,0]decane, 1,8-diazabicyclo[6,2,0]decane, 1-azabicyclo[6,1,1]decane, 1,8-diazabicyclo[6,1,1]decane, 1-azabicyclo[5,3,0]decane, 1,7-diazabicyclo[5,3,0]decane, 1-azabicyclo[5,2,1]decane, 1,7-diazabicyclo[5,2,1]decane, 1-azabicyclo[4,3,1]decane, 1,6-diazabicyclo[4,3,1]decane, 1-azabicyclo[4,2,2]decane, 1,6-diazabicyclo[4,2,2]decane, 1-azabicyclo[5,4,0]undecane, 1,7-diazabicyclo[5,4,0]undecane, 1-azabicyclo[5.3.1]undecane, 1,7-diazabicyclo[5,3,1]undecane, 1-azabicyclo[5,2,2]undecane, 1,7-diazabicyclo[5,2,2]undecane, 1-azabicyclo[4,4,1]undecane, 1,7-diazabicyclo[4,4,1]undecane, 1-azabicyclo[4,3,2]undecane, 1,7-diazabicyclo[4,3,2]undecane, 1-azabicyclo[3,3,0]octane, 1-azabicyclo[4,3,0]nonane, quinuclidine, lupinan, lupinin, quinolidine, 3-hydroxy quinuclidine, 3-quinuclidinone, quincorine, quinuclidine, cinchonidine, cinchonine, quinidine, quinine, cuprein, ibogaine, swainsonine, castanospermine, mianserin, mirtazapine, canadine, Troeger's base, a 1-azabicyclo[2,2,2]octane-3-carboxylic acid, triethylenediamine (other name: DABCO), hexamethylenetetramine, 3-quinolyldinone hydrochloride, 3-chloro-1-azabicyclo[2,2,2]octane hydrochloride, cinchonidine dihydrochloride, cinchonine hydrochloride hydrate, cinchonidine sulfonate dihydrate, hydroxynidine hydrochloride, cinchonine sulfonate dihydrate, quinine hydrochloride dihydrate, quinine sulfuric acid dihydrate, quinine phosphate, quinidine sulfonate dihydrate, mianserine hydrochloride, 1,1'-(butane-1,4-diyl)bis[4-aza-1-azoniabicyclo[2,2,2] octane] dibromide, 1,1'-(decane-1,10-diyl)bis [4-aza-1-azoniabicyclo[2,2,2]octane]dibromide, bis(trimethyl aluminum)-1,4-diazabicyclo[2,2,2] octane adduct, bismuthine, quinuclidine hydrochloride, quinuclidinone hydrochloride, 3-hydroxy quinuclidine hydrochloride, DABCO hydrochloride, quinuclidine acetate, quinuclidinone acetate, 3-hydroxy quinuclidine acetate, DABCO acetate, quinuclidine acrylate, quinuclidinone acrylate, 3-hydroxy quinuclidine acrylate, and DABCO acrylate.

Specific examples of the amidines or salts or complexes thereof include imidazole, N-methylimidazole, N-ethylimidazole, 1-benzyl-2-methylimidazole, 1-benzyl-2-phenylimidazole, 1-vinylimidazole, 1-allylimidazole, 1,8-diazabicyclo[5,4,0]undec-7-ene (other name: DBU), 1,5-diazabicyclo[4,3,0]non-5-ene (other name: DBN), N-methylimidazole hydrochloride, DBU hydrochloride, DBN hydrochloride, N-methylimidazole acetate, DBU acetate, DBN acetate, N-methylimidazole acrylate, DBU acrylate, DBN acrylate, and phthalimide DBU.

Specific examples of the compounds having a pyridine ring or salts or complexes thereof include pyridine, 2-methylpyridine, 3-methylpyridine, 4-methylpyridine, 2-ethylpyridine, 3-ethylpyridine, 4-ethylpyridine, 2-propylpyridine, 4-propylpyridine, 4-isopropylpyridine, 4-tert-butylpyridine, 4-amylpyridine, 4-(1-ethylpropyl)pyridine, 4-(5-nonyl)pyridine, 2-vinylpyridine, 2,3-dimethylpyridine, 2,4-dimethylpyridine, 2,5-dimethylpyridine, 2,6-dimethylpyridine, 3,4-dimethylpyridine, 3,5-dimethylpyridine, 3,5-diethylpyridine, N,N-dimethyl-4-aminopyridine (other name: DMAP), 2,4,6-trimethylpyridine, 2,6-di-tert-butylpyridine, N,N-dimethyl-2-aminopyridine, 4-piperidinopyridine, 4-pyrrolidinopyridine, 4-phenylpyridine, quinoline, 2-methylquinoline, 3-methylquinoline, 4-methylquinoline, 6-methylquinoline, 7-methylquinoline, 8-methylquinoline, isoquinoline, 1-methylisoquinoline, acridine, 3,4-benzoquinoline, 5,6-benzoquinoline, 7,8-benzoquinoline, 2-hydroxypyridine, 3-hydroxypyridine, 4-hydroxypyridine, 2,6-dihydroxypyridine, 2-(hydroxymethyl)pyridine, 3-(hydroxymethyl)pyridine, 4-(hydroxymethyl)pyridine, 5-hydroxyisoquinoline, 2-methoxypyridine, 3-methoxypyridine, 4-methoxypyridine, 2,6-dimethoxypyridine, 1,5-naphthiridne, 1,6-naphthiridne, 1,7-naphthiridne, 1,8-naphthiridne, 2,6-naphthiridne, 2,7-naphthiridne, 2,2'-bipyridyl, 3,3'-bipyridyl, 4,4'-bipyridyl, 2,3'-bipyridyl, 2,4'-bipyridyl, 3,4'-bipyridyl, 4,4'-ethylenedipyridine, 1,3-di(4-pyridyl)propane, 1,10-phenanthroline monohydrate, 2-(trimethylsilyl)pyridine, DMAP hydrochloride, DMAP acetate, DMAP acrylate, 1-methylpyridium chloride, 1-propylmethylpyridium chloride, borane-pyridine complex, borane-2-picoline complex, and paratoluenesulfonic acid pyridinum.

In the present invention, the catalyst A may be used either singly or in combination of two or more types. Among the catalyst A, quinuclidine, quinuclidinone, 3-hydroxy quinuclidine, DABCO, N-methylimidazole, DBU, DBN, and DMAP are preferable. In particular, quinuclidine, 3-hydroxy quinuclidine, DABCO, N-methylimidazole, DBU, and DMAP, which exhibit good reactivity for most polyhydric alcohols and are easily obtainable, are preferable.

Use amount of the catalyst A for the manufacturing method of the present invention is not particularly limited. However, the catalyst A is used preferably at from 0.0001 to 0.5 mole and more preferably at from 0.0005 to 0.2 mole per mole of hydroxyl group in the polyhydric alcohol. If it is less than 0.0001 mole, the production amount of a desired multifunctional (meth)acrylate is small. If it is more than 0.5 mole, more side products are generated and coloration of a reaction solution increases so that the purification step after completion of the reaction becomes complicated.

In the manufacturing method of the present invention, the catalyst B is one or more kinds of compounds that are selected from the group consisting of zinc-containing compounds, and examples thereof include a zinc-containing compound represent by the following General Formula (2);

[Chem. 2]

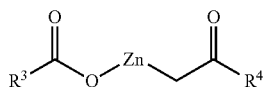

(2)

(in the formula, $R^3$ and $R^4$ are the same or different from each other and are a linear or branched alkyl group having 1 to 20 carbon atoms, a linear or branched alkenyl group having 1 to 20 carbon atoms, an aryl group having 6 to 24 carbon atoms, or a cycloalkyl group having 5 to 20 carbon atoms), a zinc-containing compound represent by the following General Formula (3);

[Chem. 3]

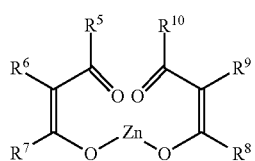

(3)

(in the formula, $R^5$, $R^6$, $R^7$, $R^8$, $R^9$, and $R^{10}$ are the same or different from each other and are a linear or branched alkyl group having 1 to 20 carbon atoms, a linear or branched alkenyl group having 1 to 20 carbon atoms, an aryl group having 6 to 24 carbon atoms, or a cycloalkyl group having 5 to 20 carbon atoms); and zinc oxalate.

Specific examples of the zinc-containing compound represented by the above General Formula (2) include zinc acetate, zinc acetate dihydrate, zinc propionate, zinc octylate, zinc neodecanoate, zinc laurate, zinc myristate, zinc stearate, cyclohexane zinc butyrate, zinc 2-ethylhexanoate, zinc benzoate, zinc tert-butylbenzoate, zinc salicylate, zinc naphthenate, zinc acrylate, and zinc methacrylate. Furthermore, when a hydrate, a solvate, or a complex with the catalyst A is present for those zinc-containing compounds, the hydrate, solvate, and complex with the catalyst A can be also used as the catalyst B of the manufacturing method of the present invention.

Specific examples of the zinc-containing compound represented by the above General Formula (3) include zinc acetylacetonate, zinc acetylacetonate hydrate, bis(2,6-dimethyl-3,5-heptanedionato) zinc, bis(2,2,6,6-tetramethyl-3,5-heptanedionato) zinc, and bis(5,5-dimethyl-2,4-hexanedionato) zinc. Furthermore, when a hydrate, a solvate, or a complex with the catalyst A is present for those zinc-containing compounds, the hydrate, solvate, and complex with the catalyst A can be also used as the catalyst B of the manufacturing method of the present invention.

In the present invention, those catalyst B may be used either singly or in combination of two or more types. Among those catalyst B, zinc acetate, zinc propionate, zinc acrylate, zinc methacrylate, and zinc acetylacetonate are preferable. In particular, zinc acetate, zinc acrylate, and zinc acetylacetonate, which exhibit good reactivity for most polyhydric alcohols and are easily obtainable, are preferable.

The use amount of the catalyst B for the manufacturing method of the present invention is not particularly limited. However, the catalyst B is used preferably at from 0.0001 to 0.5 mole and more preferably at from 0.0005 to 0.2 mole per mole of hydroxyl group in the polyhydric alcohol. If it is less than 0.0001 mole, the production amount of desired multifunctional (meth)acrylate is small. If it is more than 0.5 mole, more side products are generated and color of a reaction solution is deteriorated so that the purification step after completion of the reaction becomes complicated.

The use ratio of the catalyst A and the catalyst B for the manufacturing method of the present invention is not particularly limited. However, the catalyst A is used preferably at from 0.005 to 10.0 mole and more preferably at from 0.05 to 5.0 mole per mole of the catalyst B. If it is less than 0.005 mole, the production amount of desired multifunctional (meth)acrylate is small. If it is more than 10.0 mole, more side products are generated and color of a reaction solution is deteriorated so that the purification step after completion of the reaction becomes complicated.

As for the catalyst A and the catalyst B that are used in combination in the present invention, it is most preferable to have a combination in which the catalyst A is DABCO and the catalyst B is zinc acetate. Since the color after completion of the reaction is excellent in addition to obtaining the multifunctional (meth)acrylate with good yield, it can be preferably used for various industrial applications in which color tone is considered to be important. Furthermore, as they are a catalyst which can be obtained at relatively low cost, the manufacturing method is economically advantageous.

It is speculated that the transesterification in the manufacturing method of the present invention progresses according to the reaction pathway illustrated in FIG. 1. Firstly, as the catalyst A is added onto the carbon at β position of a monofunctional (meth)acrylate, the electron density on the carbonyl oxygen atom increases, and as the carbonyl carbon of other monofunctional (meth)acrylate is attacked by it, a reaction intermediate illustrated in FIG. 1 is generated. It is speculated that, as the intermediate induces a transesterification with a polyhydric alcohol after that, a desired multifunctional (meth)acrylate is produced. In that case, it is speculated that the catalyst B with Lewis acidity promotes the reaction pathway illustrated in FIG. 1 by activating the (meth)acryloyl group.

The catalyst A and the catalyst B that are used in the present invention may be added from the beginning of the reaction or during the reaction. Furthermore, a desired use amount may be added in bulk or in divided portions. Furthermore, when the catalyst A and/or the catalyst B are/is a solid, they/it may be added after being dissolved in a solvent.

The reaction temperature for the manufacturing method of the present invention is preferably from 40 to 180° C. and particularly preferably from 60 to 160° C. When the reaction temperature is lower than 40° C., the reaction rate is extremely slow. When it is higher than 180° C., thermal polymerization of the (meth)acryloyl group may occur or color of the reaction solution is deteriorated so that the purification step after completion of the reaction becomes complicated.

The reaction pressure for the manufacturing method of the present invention is not particularly limited as long as a pre-determined reaction temperature can be maintained. The reaction may be performed in a state with reduced pressure or in a pressurized state. In general, it is 0.000001 to 10 MPa (absolute pressure).

In the manufacturing method of the present invention, a monohydric alcohol derived from monofunctional (meth)acrylate is generated as a side product in accordance with progress of the transesterification. Although it is possible that the monohydric alcohol is co-present in the reaction system, the transesterification can be further promoted by discharging the monohydric alcohol to outside.

In the manufacturing method of the present invention, inert gas such as argon, helium, nitrogen, or carbon dioxide gas may be introduced to the inside of a system for the purpose of maintaining the color of a reaction solution at good level. However, for the purpose of preventing polymerization of the (meth)acryloyl group, oxygen-containing gas may be introduced to the inside of a system. Specific examples of the oxygen-containing gas include a mixture gas of air, a mixture gas of oxygen and nitrogen and a mixture gas of oxygen and helium. As for the method for introducing oxygen-containing gas, there is a method in which the gas is dissolved in a reaction solution or a method in which the gas is bubbled into a reaction solution (so-called bubbling).

In the manufacturing method of the present invention, it is desirable to add a polymerization inhibitor to an inside of a system for the purpose of preventing the polymerization of a (meth)acryloyl group. Specific examples of the polymerization inhibitor include an organic polymerization inhibitor such as hydroquinone, tert-butylhydroquinone, hydroquinone monomethyl ether, 2,6-di-tert-butyl-4-methylphenol, 2,4,6-tri-tert-butylphenol, 4-tert-butylcatechol, benzoquinone, phenothiazine, N-Nitroso-N-phenylhydroxylamine ammonium, 2,2,6,6-tetramethylpiperidine-1-oxyl, or 4-hydroxy-2,2,6,6-tetramethylpiperidine-1-oxyl, an inorganic polymerization inhibitor such as copper chloride or copper sulfate, and an organic salt-based polymerization inhibitor such as dibutyl dithiocarbamic acid copper or N-nitroso-N-phenylhydroxylamine aluminum salt. The polymerization inhibitor may be added either singly or in combination of two or more types. It may be added from the beginning of the reaction or during the reaction. Furthermore, a desired use amount may be added in bulk or in divided portions. Furthermore, it may be added continuously via a rectification tower. The addition amount of the polymerization inhibitor is preferably from 5 to 30,000 wtppm and more preferably from 25 to 10,000 wtppm in a reaction solution. If it is less than 5 wtppm, the effect of polymerization inhibition is insufficient. If it is more than 30,000 wtppm, color of the reaction solution is deteriorated or curing rate of a multifunctional (meth)acrylate to be obtained is lowered so that the purification step after completion of the reaction becomes complicated.

The reaction time for the manufacturing method of the present invention may vary depending on the type and use amount of a catalyst, reaction temperature, reaction pressure, and the like. However, it is generally from 0.1 to 150 hours, and preferably from 0.5 to 80 hours.

The manufacturing method of the present invention can be carried out by any of the batch method, semi-batch method, and continuous method. As an example of the batch method, the method can be carried out as follows: a polyhydric alcohol, a monofunctional (meth)acrylate, a catalyst, and a polymerization inhibitor are injected to a reaction vessel and, under bubbling of oxygen-containing gas into the reaction solution, they are stirred at pre-determined temperature, and after that, by extracting from the reaction vessel at pre-determined pressure the monohydric alcohol which is generated in accordance with progress of the transesterification, a desired multifunctional (meth)acrylate can be produced.

For the reaction product which is obtained by the manufacturing method of the present invention by performing a separation and purification operation in which an operation for crystal precipitation such as crystal precipitation by cooling or crystal precipitation by concentration, an operation of filtering such as filtering under pressure, filtering with aspiration, or filtering with centrifuge, an operation of distillation such as pot still distillation, fractional distillation, molecular distillation, or water vapor distillation, an operation of extraction such as solid-liquid extraction or liquid-liquid extraction, or decantation are combined, a desired multifunctional (meth)acrylate can be obtained with high purity. For the separation and purification operation, a solvent may be used. Furthermore, it is also possible to use a neutralizing agent for neutralizing the catalyst and/or polymerization inhibitor used in the present invention, an adsorbing agent for adsorptive removal, an acid and/or an alkali for dissociating or removing side products, active charcoal for improving the color, and silious earth for enhancing the filtering efficiency or filtering rate.

EXAMPLES

Hereinbelow, the present invention is described in more detail in view of Examples and Comparative Examples, but the present invention is not limited to Examples as long as it remains within the gist of the present invention. Furthermore, if not particularly described otherwise, the expression "parts" means "parts by mass" and the expression "%" means "% by mass" hereinbelow.

The reaction yield of Examples and Comparative Examples was obtained by quantifying the monohydric alcohol which is produced according to the progress of a transesterification and performing the calculation using the following equation. Furthermore, quantification of the monohydric alcohol was performed by an internal standard method using high performance liquid chromatograph equipped with refractive index detector (column: Atlantis (Part No. 186003748, inner diameter of column: 4.6 mm, column length: 250 mm) manufactured by Nihon waters K.K., solvent: pure water or 10% by volume of aqueous solution of isopropanol).

Reaction yield (mole %)=Mole number of monohydric alcohol generated according to progress of transesterification/(Mole number of polyhydric alcohol used as raw material×Number of hydroxyl groups contained in polyhydric alcohol)×100

The purification yield of Examples and Comparative Examples was obtained after performing a separation and purification operation like distillation, crystal precipitation, and filtration for a reaction product after completion of the transesterification. Calculation was made by using the weight of a purified product containing multifunctional (meth)acrylate.

Purification yield (%)=Purified product containing multifunctional (meth)acrylate (parts)/(Molecular weight of multifunctional (meth)acrylate which is generated when all hydroxyl groups in polyhydric alcohol used as a raw material are (meth)acrylated×Mole number of polyhydric alcohol used as raw material)×100

In Examples and Comparative Examples, determination of the presence of desired multifunctional (meth)acrylate in a reaction product and purified product was performed by using a high performance liquid chromatograph equipped with a UV detector (column: ACQUITY UPLC BEH C18 (Part No. 186002350, inner diameter of column: 2.1 mm, column length: 50 mm) manufactured by Nihon waters K.K., wavelength for detection: 210 nm, solvent: mixed solvent of 0.03% by weight aqueous solution of trifluoroacetic acid and methanol).

Example 1

To a 20 milliliter test tube equipped with a stirring bar, a thermometer, an inlet for gas introduction, and a condenser, 0.533 part (0.0039 mole) of pentaerythritol, 5.308 parts (0.0408 mole) of 2-methoxyethyl acrylate, 0.016 part (0.0001 mole) of quinuclidine as the catalyst A, 0.025 part (0.0001 mole) of zinc acetate as the catalyst B, and 0.012 part (2036 wtppm relative to total weight of injected raw materials) of hydroquinone monomethyl ether were injected. Reflux under heating with reaction liquid temperature in the range of from 105 to 120° C. was performed for 5 hours while oxygen-containing gas (5% by volume of oxygen and 95% by volume of nitrogen) is bubbled in the liquid. After that, 2-methoxyethanol contained in the reaction solution, which has been generated in accordance with the transesterification, was quantified, and as a result, the reaction yield was found to be 48%. By using a high performance liquid chromatograph equipped with an UV detector, composition of the reaction product contained the reaction solution was analyzed. As a result, it was confirmed that pentaerythritol diacrylate, pentaerythritol triacrylate, and pentaerythritol tetraacrylate are contained as a main component.

Examples 2 to 22 and Comparative Examples 1 to 18

The transesterification was performed by the same method as Example 1 while modifying the polyhydric alcohol, monofunctional (meth)acrylate, the catalyst A, the catalyst B, reaction temperature, and reaction time, and the reaction yield was calculated. The results are shown in Table 1 to Table 7. Furthermore, the following abbreviations were used in the tables.
PET: pentaerythritol
MCA: 2-methoxyethyl acrylate
QD: quinuclidine
$Zn(OAc)_2$: zinc acetate
HQD: 3-hydroxy quinuclidine
DABCO: triethylenediamine
NMI: N-methylimidazole
DBU: 1,8-diazabicyclo[5,4,0]undec-7-ene
DBN: 1,5-diazabicyclo[4,3,0]non-5-ene
DMAP: N,N-dimethyl-4-aminopyridine
$Zn(acac)_2$: zinc acetylacetonate
DPET: dipentaerythritol
DTMP: ditrimethylolpropane
GLY: glycerin
THEIC: tris(2-hydroxyethyl)isocyanurate
DIGLY: diglycerin
PET-4EO: ethylene oxide adduct of pentaerythritol (hydroxyl value: 717 mgKOH/g)
DPET-6PO: ethylene oxide adduct of dipentaerythritol (hydroxyl value: 643 mgKOH/g)
TMHD: N,N,N',N'-tetramethyl-1,6-hexanediamine
BA: n-butyl acrylate
TEA: triethanolamine Example 23

To a 1 liter flask equipped with a stirrer, a thermometer, an inlet for gas introduction, a rectification tower, and a condenser, 69.33 parts (0.51 mole) of pentaerythritol, 690.05 parts (5.30 mole) of 2-methoxyethyl acrylate, 2.04 parts (0.02 mole) of DABCO as the catalyst A, 3.26 parts (0.02 mole) of zinc acetate as the catalyst B, and 1.56 parts (2036 wtppm relative to total weight of injected raw materials) of hydroquinone monomethyl ether were injected. Oxygen-containing gas (5% by volume of oxygen and 95% by volume of nitrogen) was bubbled in the liquid. Pressure inside the reaction system was adjusted within a range of from 130 to 760 mmHg under heating and stirring with reaction liquid temperature in the range of from 105 to 120° C. A mixture liquid of 2-methoxyethanol and 2-methoxyethyl acrylate, which has been generated in accordance with the transesterification, was withdrawn from the reaction system via the rectification tower and condenser. In addition, 2-methoxyethyl acrylate in the same parts by weight as the withdrawn solution was added from time to time to the reaction system. As a result of quantifying the 2-methoxyethanol contained in the solution withdrawn from the reaction system, it was found that the reaction yield was 88% after 30 hours from the start of the heating and stirring. Thus, heating of the reaction solution was terminated and, simultaneously, the pressure inside the reaction system was brought back to atmospheric pressure to complete the withdrawing. The reaction solution was cooled to room temperature, and after separating 3.89 parts of precipitates by filtration, distillation under reduced pressure was carried out for 8 hours at temperature of 70 to 95° C. and pressure range of from 0.001 to 100 mmHg while dry air is bubbled in the filtered solution. Accordingly, a distilled extract liquid containing unreacted 2-methoxyethyl acrylate was separated. By using a high performance liquid chromatograph equipped with an UV detector, composition of the residual liquid after distillation under reduced pressure was analyzed. As a result, it was confirmed that pentaerythritol triacrylate and pentaerythritol tetraacrylate are contained as a main component. The purification yield which is obtained by taking the above residual liquid as a purified product was found to be 96%. The results are shown in Table 8.

Example 24

To a 1 liter flask equipped with a stirrer, a thermometer, an inlet for gas introduction, a rectification tower, and a condenser, 86.33 parts (0.34 mole) of dipentaerythritol, 690.05 parts (5.30 mole) of 2-methoxyethyl acrylate, 4.08 parts (0.04 mole) of DABCO as the catalyst A, 6.52 parts (0.04 mole) of zinc acetate as the catalyst B, and 1.63 parts (2061 wtppm relative to total weight of injected raw materials) of hydroquinone monomethyl ether were injected. Oxygen-containing gas (5% by volume of oxygen and 95% by volume of nitrogen) was bubbled in the liquid. Pressure inside the reaction system was adjusted within a range of from 250 to 760 mmHg under heating and stirring with reaction liquid temperature in the range of from 120 to 145° C. A mixture liquid of 2-methoxyethanol and 2-methoxyethyl acrylate, which has been generated in accordance with the transesterification, was withdrawn from the reaction system via the rectification tower and condenser. In addition, 2-methoxyethyl acrylate in the same parts by weight as the withdrawn solution was added from time to time to the reaction system. As a result of quantifying the 2-methoxyethanol contained in the solution withdrawn from the reaction system, it was found that the reaction yield was 86% after 24 hours from start of the heating and stirring. Thus, heating of the reaction solution was terminated and, simultaneously, the pressure inside the reaction system was brought back to atmospheric pressure to complete the withdrawing. The reaction solution was cooled to room temperature, and after separating 8.38 parts of precipitates by filtration, distillation under reduced pressure was for 8 hours at temperature of 70 to 95° C. and pressure range of from 0.001 to 100 mmHg while dry air is bubbled in the filtered solution. Accordingly, a distilled extract liquid containing unreacted 2-methoxyethyl acrylate was separated. By using a high performance liquid chromatograph equipped with an UV detector, composition of the residual liquid after distillation under reduced pressure was analyzed. As a result, it was confirmed that dipentaerythritol pentaacrylate and dipentaerythritol hexaacrylate are contained as a main component. The purification yield which is obtained by taking the above residual liquid as a purified product was found to be 99%. The results are shown in Table 8.

TABLE 1

| | Polyhydric alcohol | Monofunctional (meth)acrylate | Catalyst A | Catalyst B | Reaction temperature [° C.] | Reaction time [hr] | Reaction yield [%] |
|---|---|---|---|---|---|---|---|
| Example 1 | PET: 0.533 Parts (0.0039 Mole) | MCA: 5.308 Parts (0.0408 Mole) | QD: 0.016 Parts (0.0001 Mole) | Zn(OAc)$_2$: 0.025 Parts (0.0001 Mole) | 105 to 120 | 5 | 48 |
| Example 2 | PET: 0.533 Parts (0.0039 Mole) | MCA: 5.308 Parts (0.0408 Mole) | HQD: 0.018 Parts (0.0001 Mole) | Zn(OAc)$_2$: 0.025 Parts (0.0001 Mole) | 105 to 120 | 7 | 40 |
| Example 3 | PET: 0.533 Parts (0.0039 Mole) | MCA: 5.308 Parts (0.0408 Mole) | DABCO: 0.016 Parts (0.0001 Mole) | Zn(OAc)$_2$: 0.025 Parts (0.0001 Mole) | 105 to 120 | 7 | 30 |
| Example 4 | PET: 0.533 Parts (0.0039 Mole) | MCA: 5.308 Parts (0.0408 Mole) | NMI: 0.011 Parts (0.0001 Mole) | Zn(OAc)$_2$: 0.025 Parts (0.0001 Mole) | 105 to 120 | 7 | 27 |
| Example 5 | PET: 0.533 Parts (0.0039 Mole) | MCA: 5.308 Parts (0.0408 Mole) | DBU: 0.021 Parts (0.0001 Mole) | Zn(OAc)$_2$: 0.025 Parts (0.0001 Mole) | 105 to 120 | 5 | 49 |

TABLE 2

| | Polyhydric alcohol | Monofunctional (meth)acrylate | Catalyst A | Catalyst B | Reaction temperature [° C.] | Reaction time [hr] | Reaction yield [%] |
|---|---|---|---|---|---|---|---|
| Example 6 | PET: 0.533 Parts (0.0039 Mole) | MCA: 5.308 Parts (0.0408 Mole) | DBN: 0.017 Parts (0.0001 Mole) | Zn(OAc)$_2$: 0.025 Parts (0.0001 Mole) | 105 to 120 | 7 | 35 |
| Example 7 | PET: 0.533 Parts (0.0039 Mole) | MCA: 5.308 Parts (0.0408 Mole) | DMAP: 0.017 Parts (0.0001 Mole) | Zn(OAc)$_2$: 0.025 Parts (0.0001 Mole) | 105 to 120 | 7 | 27 |
| Example 8 | PET: 0.533 Parts (0.0039 Mole) | MCA: 5.308 Parts (0.0408 Mole) | DABCO: 0.016 Parts (0.0001 Mole) | Zn(acac)$_2$: 0.036 Parts (0.0001 Mole) | 105 to 120 | 7 | 39 |
| Example 9 | DPET: 0.664 Parts (0.0026 Mole) | MCA: 5.308 Parts (0.0408 Mole) | DABCO: 0.031 Parts (0.0003 Mole) | Zn(OAc)$_2$: 0.050 Parts (0.0003 Mole) | 120 to 145 | 10 | 45 |
| Example 10 | DTMP: 0.981 Parts (0.0039 Mole) | MCA: 5.308 Parts (0.0408 Mole) | DABCO: 0.016 Parts (0.0001 Mole) | Zn(OAc)$_2$: 0.025 Parts (0.0001 Mole) | 105 to 120 | 7 | 35 |

TABLE 3

| | Polyhydric alcohol | Monofunctional (meth)acrylate | Catalyst A | Catalyst B | Reaction temperature [° C.] | Reaction time [hr] | Reaction yield [%] |
|---|---|---|---|---|---|---|---|
| Example 11 | GLY: 0.537 Parts (0.0061 Mole) | MCA: 6.050 Parts (0.0465 Mole) | DBU: 0.019 Parts (0.0001 Mole) | Zn(acac)$_2$: 0.032 Parts (0.0001 Mole) | 105 to 120 | 7 | 30 |
| Example 12 | THEIC: 1.581 Parts (0.0061 Mole) | MCA: 6.145 Parts (0.0472 Mole) | DABCO: 0.014 Parts (0.0001 Mole) | Zn(OAc)$_2$: 0.023 Parts (0.0001 Mole) | 105 to 120 | 7 | 47 |
| Example 13 | DIGLY: 0.651 Parts (0.0039 Mole) | MCA: 5.308 Parts (0.0408 Mole) | DABCO: 0.016 Parts (0.0001 Mole) | Zn(acac)$_2$: 0.025 Parts (0.0001 Mole) | 105 to 120 | 7 | 32 |
| Example 14 | PET-4EO: 1.104 Parts (0.0035 Mole) | MCA: 4.777 Parts (0.0367 Mole) | DABCO: 0.014 Parts (0.0001 Mole) | Zn(OAc)$_2$: 0.023 Parts (0.0001 Mole) | 105 to 120 | 7 | 38 |
| Example 15 | DPET-6EO: 1.162 Parts (0.0022 Mole) | MCA: 4.512 Parts (0.0347 Mole) | DABCO: 0.013 Parts (0.0001 Mole) | Zn(OAc)$_2$: 0.021 Parts (0.0001 Mole) | 105 to 120 | 7 | 34 |
| Example 16 | PET: 0.533 Parts (0.0039 Mole) | BA: 5.308 Parts (0.0414 Mole) | DABCO: 0.016 Parts (0.0001 Mole) | Zn(OAc)$_2$: 0.025 Parts (0.0001 Mole) | 120 to 135 | 10 | 19 |

TABLE 4

| | Polyhydric alcohol | Monofunctional (meth)acrylate | Catalyst A | Catalyst B | Reaction temperature [° C.] | Reaction time [hr] | Reaction yield [%] |
|---|---|---|---|---|---|---|---|
| Example 17 | PET: 0.533 Parts (0.0039 Mole) | MCA: 5.308 Parts (0.0408 Mole) | DABCO: 0.016 Parts (0.0001 Mole) | Zinc propionate: 0.029 Parts (0.0001 Mole) | 105 to 120 | 7 | 45 |
| Example 18 | PET: 0.533 Parts (0.0039 Mole) | MCA: 5.308 Parts (0.0408 Mole) | DABCO: 0.031 Parts (0.0003 Mole) | Zinc acrylate: 0.028 Parts (0.0001 Mole) | 105 to 120 | 7 | 33 |
| Example 19 | PET: 0.533 Parts (0.0039 Mole) | MCA: 5.308 Parts (0.0408 Mole) | DABCO: 0.031 Parts (0.0003 Mole) | Zinc octylate: 0.048 Parts (0.0001 Mole) | 105 to 120 | 7 | 26 |
| Example 20 | xylitol: 0.713 Parts (0.0047 Mole) | MCA: 5.496 Parts (0.0422 Mole) | DABCO: 0.031 Parts (0.0003 Mole) | Zn(OAc)$_2$: 0.101 Parts (0.0006 Mole) | 120 to 145 | 5 | 29 |
| Example 21 | D-sorbitol: 0.712 Parts (0.0039 Mole) | MCA: 5.496 Parts (0.0422 Mole) | DABCO: 0.031 Parts (0.0003 Mole) | Zn(OAc)$_2$: 0.101 Parts (0.0006 Mole) | 120 to 145 | 7 | 18 |
| Example 22 | TEA: 1.084 Parts (0.0073 Mole) | MCA: 5.114 Parts (0.0393 Mole) | DABCO: 0.007 Parts (0.0001 Mole) | Zn(OAc)$_2$: 0.024 Parts (0.0001 Mole) | 105 to 120 | 5 | 35 |

TABLE 5

| | Polyhydric alcohol | Monofunctional (meth)acrylate | Catalyst A | Catalyst B | Reaction temperature [° C.] | Reaction time [hr] | Reaction yield [%] |
|---|---|---|---|---|---|---|---|
| Comparative Example 1 | PET: 0.533 Parts (0.0039 Mole) | MCA: 5.308 Parts (0.0408 Mole) | QD: 0.016 Parts (0.0001 Mole) | | 105 to 120 | 7 | 5 |
| Comparative Example 2 | PET: 0.533 Parts (0.0039 Mole) | MCA: 5.308 Parts (0.0408 Mole) | HQD: 0.018 Parts (0.0001 Mole) | | 105 to 120 | 7 | 5 |
| Comparative Example 3 | PET: 0.533 Parts (0.0039 Mole) | MCA: 5.308 Parts (0.0408 Mole) | DABCO: 0.016 Parts (0.0001 Mole) | | 105 to 120 | 7 | 3 |
| Comparative Example 4 | PET: 0.533 Parts (0.0039 Mole) | MCA: 5.308 Parts (0.0408 Mole) | NMI: 0.011 Parts (0.0001 Mole) | | 105 to 120 | 7 | 2 |
| Comparative Example 5 | PET: 0.533 Parts (0.0039 Mole) | MCA: 5.308 Parts (0.0408 Mole) | DBU: 0.021 Parts (0.0001 Mole) | | 105 to 120 | 7 | 11 |
| Comparative Example 6 | PET: 0.533 Parts (0.0039 Mole) | MCA: 5.308 Parts (0.0408 Mole) | DBN: 0.017 Parts (0.0001 Mole) | | 105 to 120 | 7 | 5 |

TABLE 6

|  | Polyhydric alcohol | Monofunctional (meth)acrylate | Catalyst A | Catalyst B | Reaction temperature [° C.] | Reaction time [hr] | Reaction yield [%] |
|---|---|---|---|---|---|---|---|
| Comparative Example 7 | PET: 0.533 Parts (0.0039 Mole) | MCA: 5.308 Parts (0.0408 Mole) | DMAP: 0.017 Parts (0.0001 Mole) |  | 105 to 120 | 7 | 3 |
| Comparative Example 8 | PET: 0.533 Parts (0.0039 Mole) | MCA: 5.308 Parts (0.0408 Mole) |  | Zn(OAc)$_2$: 0.025 Parts (0.0001 Mole) | 105 to 120 | 7 | 3 |
| Comparative Example 9 | PET: 0.533 Parts (0.0039 Mole) | MCA: 5.308 Parts (0.0408 Mole) |  | Zn(acac)$_2$: 0.036 Parts (0.0001 Mole) | 105 to 120 | 7 | 2 |
| Comparative Example 10 | PET: 0.533 Parts (0.0039 Mole) | MCA: 5.308 Parts (0.0408 Mole) | n-Hexylamine: 0.014 Parts (0.0001 Mole) | Zn(OAc)$_2$: 0.025 Parts (0.0001 Mole) | 105 to 120 | 7 | 5 |
| Comparative Example 11 | PET: 0.533 Parts (0.0039 Mole) | MCA: 5.308 Parts (0.0408 Mole) | Benzylamine: 0.015 Parts (0.0001 Mole) | Zn(OAc)$_2$: 0.025 Parts (0.0001 Mole) | 105 to 120 | 7 | 4 |
| Comparative Example 12 | PET: 0.533 Parts (0.0039 Mole) | MCA: 5.308 Parts (0.0408 Mole) | Cyclohexylamine: 0.015 Parts (0.0001 Mole) | Zn(OAc)$_2$: 0.025 Parts (0.0001 Mole) | 105 to 120 | 7 | 7 |

TABLE 7

|  | Polyhydric alcohol | Monofunctional (meth)acrylate | Catalyst A | Catalyst B | Reaction temperature [° C.] | Reaction time [hr] | Reaction yield [%] |
|---|---|---|---|---|---|---|---|
| Comparative Example 13 | PET: 0.533 Parts (0.0039 Mole) | MCA: 5.308 Parts (0.0408 Mole) | TMHD: 0.012 Parts (0.0001 Mole) | Zn(OAc)$_2$: 0.025 Parts (0.0001 Mole) | 105 to 120 | 7 | 9 |
| Comparative Example 14 | PET: 0.533 Parts (0.0039 Mole) | MCA: 5.308 Parts (0.0408 Mole) | 1,4-Dimethyl piperazine: 0.016 Parts (0.0001 Mole) | Zn(OAc)$_2$: 0.025 Parts (0.0001 Mole) | 105 to 120 | 7 | 7 |
| Comparative Example 15 | PET: 0.533 Parts (0.0039 Mole) | BA: 5.308 Parts (0.0414 Mole) | DABCO: 0.016 Parts (0.0001 Mole) |  | 120 to 135 | 10 | 0 |
| Comparative Example 16 | PET: 0.533 Parts (0.0039 Mole) | BA: 5.308 Parts (0.0414 Mole) |  | Zn(OAc)$_2$: 0.025 Parts (0.0001 Mole) | 120 to 135 | 10 | 0 |
| Comparative Example 17 | PET: 0.533 Parts (0.0039 Mole) | MCA: 5.308 Parts (0.0408 Mole) | Tetra-normal butyl-1,3-dilauryloxydistannoxane: 0.060 Parts (0.0001 Mole) |  | 105 to 120 | 8 | 3 |
| Comparative Example 18 | PET: 0.533 Parts (0.0039 Mole) | MCA: 5.308 Parts (0.0408 Mole) | Titanium tetranormal butoxide: 0.053 Parts (0.0002 Mole) |  | 105 to 120 | 6 | 0 |

TABLE 8

|  | Polyhydric alcohol | Monofunctional (meth)acrylate | Catalyst A | Catalyst B | Reaction temperature [° C.] | Reaction time [hr] | Reaction yield [%] | Purification yield [%] |
|---|---|---|---|---|---|---|---|---|
| Example 23 | PET: 69.33 Parts (0.51 Mole) | MCA: 690.05 Parts (5.30 Mole) | DABCO: 2.04 Parts (0.02 Mole) | Zn(OAc)$_2$: 3.26 Parts (0.02 Mole) | 105 to 120 | 30 | 88 | 96 |
| Example 24 | DPET: 86.33 Parts (0.34 Mole) | MCA: 690.05 Parts (5.30 Mole) | DABCO: 4.08 Parts (0.04 Mole) | Zn(OAc)$_2$: 6.52 Parts (0.04 Mole) | 120 to 145 | 24 | 86 | 99 |

From each example in which the catalyst A and the catalyst B of the present invention are used in combination, the desired multifunctional (meth)acrylate can be obtained with good yield compared to Comparative Example in which only one of the catalyst A and the catalyst B is used, Comparative Example in which the catalyst B is used in combination with a primary amine or a chain type tertiary amine, and Comparative Example in which, as a technique of prior art, an organotin compound or a titanium compound is used as a catalyst. Thus, the effect of the present invention based on the combined use of the catalyst A and the catalyst B is quite excellent.

INDUSTRIAL APPLICABILITY

According to the method of the present invention, a multifunctional (meth)acrylate can be obtained with good yield from a polyhydric alcohol and a monofunctional (meth)acrylate. The multifunctional (meth)acrylate obtained by the manufacturing method of the present invention can be desirably used for various industrial applications as a cross-linking component in paint, ink, adhesives, optical lens, a filling agent, and a blend like a molding material, or as a reactive diluent component.

The invention claimed is:

1. A multifunctional (meth)acrylate manufacturing method, wherein the following Catalyst A and Catalyst B are used in combination for manufacturing a multifunctional (meth)acrylate by a transesterification of a polyhydric alcohol having 3 or more alcoholic hydroxyl groups and a monofunctional (meth)acrylate:

Catalyst A: one or more kinds of compounds selected from the group consisting of cyclic tertiary amines with an azabicyclo structure or salts or complexes thereof, amidines or salts or complexes thereof, and compounds with a pyridine ring or salts or complexes thereof, Catalyst B: one or more kinds of compounds selected from the group consisting of zinc-containing compounds represented by the following General Formula (2) and/or General Formula (3):

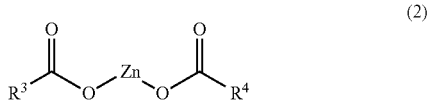

(2)

wherein $R^3$ and $R^4$ are the same or different from each other and are a linear or branched alkyl group having 1 to 20 carbon atoms, a linear or branched alkenyl group having 1 to 20 carbon atoms, an aryl group having 6 to 24 carbon atoms, or a cycloalkyl group having 5 to 20 carbon atoms,

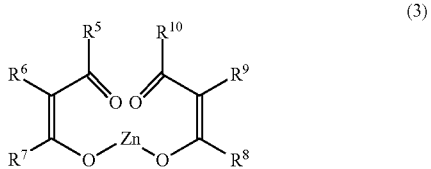

(3)

wherein $R^5$, $R^6$, $R^7$, $R^8$, $R^9$, and $R^{10}$ are the same or different from each other and are a linear or branched alkyl group having 1 to 20 carbon atoms, a linear or branched alkenyl group having 1 to 20 carbon atoms, an aryl group having 6 to 24 carbon atoms, or a cycloalkyl group having 5 to 20 carbon atoms, $R^6$ and $R^9$ may be a hydrogen atom.

2. The multifunctional (meth)acrylate manufacturing method according to claim 1, wherein the polyhydric alcohol is any one of trimethylolethane, trimethylolpropane, glycerin, an alkylene oxide adduct of glycerin, tris(2-hydroxyethyl)isocyanurate, triethanolamine, ditrimethylolethane, ditrimethylolpropane, diglycerin, an alkylene oxide adduct of diglycerin, pentaerythritol, an alkylene oxide adduct of pentaerythritol, xylitol, dipentaerythritol, an alkylene oxide adduct of dipentaerythritol, and Dsorbitol.

3. The multifunctional (meth)acrylate manufacturing method according to claim 1, wherein the polyhydric alcohol is pentaerythritol or dipentaerythritol.

4. The multifunctional (meth)acrylate manufacturing method according to claim 1, wherein the monofunctional (meth)acrylate is any one of methyl acrylate, ethyl acrylate, n-butyl acrylate, i-butyl acrylate, and 2-methoxyethyl acrylate.

5. The multifunctional (meth)acrylate manufacturing method according to claim 1, wherein the monofunctional (meth)acrylate is 2-methoxyethyl acrylate.

6. The multifunctional (meth)acrylate manufacturing method according to claim 1, wherein the Catalyst A is any one of quinuclidine, 3-hydroxy quinuclidine, triethylenediamine, N-methylimidazole, 1,8-diazabicyclo[5,4,0]undec-7-ene, and N,N-dimethyl-4-aminopyridine.

7. The multifunctional (meth)acrylate manufacturing method according to claim 1, wherein the Catalyst B is any one of zinc acetate, zinc propionate, zinc acrylate, zinc methacrylate, and zinc acetylacetonate.

8. The multifunctional (meth)acrylate manufacturing method according to claim 1, wherein the Catalyst A is triethylenediamine and the Catalyst B is zinc acetate.

9. The multifunctional (meth)acrylate manufacturing method according to claim 1, wherein
the amount of each of the Catalyst A and the Catalyst B are 0.0001 to 0.5 mole with respect to 1 mole of the alcoholic hydroxyl group of the polyhydric alcohol having 3 or more alcoholic hydroxyl groups, and
the amount of the Catalyst A is 0.005 to 10.0 mole with respect to 1 mole of the Catalyst B.

* * * * *